United States Patent

Morgan

Patent Number: 5,489,305
Date of Patent: Feb. 6, 1996

[54] MANDIBULAR PROSTHESES

[75] Inventor: Frank H. Morgan, Las Vegas, Nev.

[73] Assignee: TiMesh, Inc., Las Vegas, Nev.

[21] Appl. No.: 317,185

[22] Filed: Oct. 3, 1994

[51] Int. Cl.$^6$ .................................................. A61F 2/30
[52] U.S. Cl. ............................................. 623/16; 623/18
[58] Field of Search ........................... 623/11, 16, 18, 623/22, 23; 606/60

[56] References Cited

U.S. PATENT DOCUMENTS

| | | | |
|---|---|---|---|
| 3,488,779 | 1/1970 | Christensen | 623/18 |
| 3,720,959 | 3/1973 | Hahn | 623/16 |
| 4,693,722 | 9/1987 | Wall | 623/18 |
| 4,726,808 | 2/1988 | Collins | 623/16 |
| 4,778,472 | 10/1988 | Homsy et al. | 623/18 |
| 4,917,701 | 4/1990 | Morgan | 623/18 X |
| 5,092,883 | 3/1992 | Eppley et al. | 623/11 |
| 5,139,497 | 8/1992 | Tilghman et al. | 623/16 X |

FOREIGN PATENT DOCUMENTS

| | | | |
|---|---|---|---|
| 848005 | 7/1981 | U.S.S.R. | 623/18 |
| 9216170 | 10/1992 | WIPO | 623/18 |

Primary Examiner—Mary Beth O. Jones
Attorney, Agent, or Firm—Philip D. Junkins

[57] ABSTRACT

Mandibular prosthesis apparatus for mounting on the remaining stump portion of the ascending ramus, at the posterior end of a human mandible, from which has been removed by surgical intervention a diseased or fractured condylar process portion of the ramus as part of the temporomandibular (TM) joint complex of the mandible. The prosthesis apparatus consists of: a synthetic condylar replacement member which is formed of non-toxic, biocompatible Delrin acetal resin and includes an upper knob-shaped condyle portion and a lower cylindrical condyle-supporting stem portion; and a ramus attachment fixture which includes a cylindrical sleeve portion for receiving the cylindrical condyle-supporting stem portion of the condylar replacement member and a mounting panel for attaching the fixture to the stump portion of the ramus. The ramus attachment fixture is formed of tissue-biocompatible, perforated titanium sheet material. Bone screws, applied through the perforations of the titanium sheet material, affix the ramus attachment fixture, via its mounting panel, to the ramus stump and secure the stem portion of the synthetic condylar replacement member within the cylindrical sleeve portion of the attachment fixture to maintain proper orientation of the knob-shaped condyle portion of the replacement member within the TM joint complex of the mandible.

5 Claims, 1 Drawing Sheet

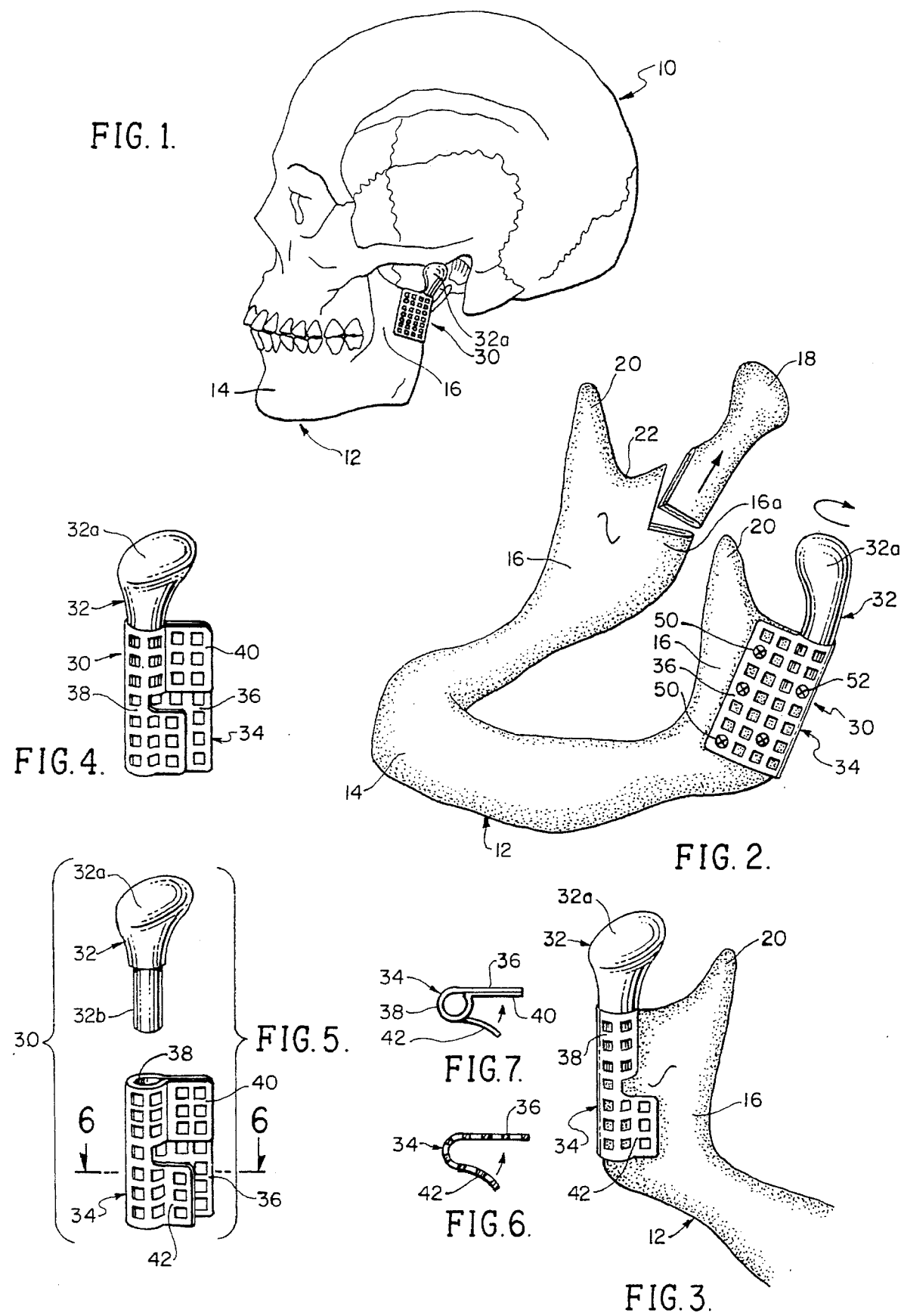

MANDIBULAR PROSTHESES

BACKGROUND OF THE INVENTION

1. Field of the Invention

The Present invention relates to the field of human mandibular prostheses. More particularly, the invention relates to improved prosthetic apparatus for the repair and/or replacement of the condylar process of the human mandible.

2. Description of the Prior Art

The human mandible is a U-shaped bone (lower jaw bone) having a generally horizontal body portion with an anterior prominence (mandibular symphysis) defining the chin in the facial structure. A posterior branch or ramus extends upwardly and rearwardly from each end of the body portion. The upper end of each ramus terminates in a forward coronoid process and a rearward condyloid process or condyle. The condyle is a knob-shaped prominence which fits into a cup-shaped socket known as the glencid fossa formed in the temporal bone of the skull. The condyle, glenoid fossa, and supporting muscle tissue on each side of the skull define a temporomandibular joint (TMJ) which permits the lower jaw to be freely movable.

Surgery in the area of the TM joints of the human mandible frequently involves the necessity of total replacement of the condyle head or entire condylar process of the right or left side or both sides of the mandible. Such surgeries may involve arthroplasty for advanced degenerative TM joint disease, repair and reconstruction of ankylosed TM joints, repair of traumatic fractures of the condyle resulting in loss of normal condylar structure and function, and surgical treatment of congenital hypoplasia of the ramus and condylar process.

A number of types of metallic alloplastic materials have been utilized in the past for mandibular condylar replacements including chrome-cobalt alloys, pure titanium and titanium alloys and stainless steel. In addition, Proplast, Teflon, Silastic, and other synthetic alloplastic materials have been utilized in an effort to obtain maximal function, anatomic reproduction and long life of TM joint replacement protheses. Clinical reports have indicated that metallic condyle replacement prostheses have produced bone loss and erosion of the interfacing surface of the cup-shaped glenoid fossa. Other adverse clinical reports have resulted where Proplast, Teflon and Silastic synthetic materials have been used to form condyle replacement prostheses and such materials have been rejected by the TMJ environment frequently resulting in irreparable harm and damage to the TM joint complex.

In U.S. Pat. No. 3,720,959, granted in 1973 to G. W. Hahn, there is disclosed mandibular prosthetic appliances constructed of malleable metal mesh material, particularly stainless steel mesh fabricated by casting. Where the Hahn mandibular prostheses involve replacement of the condyle such component is fabricated of an acrylic resin material and formed about, and secured to, a metallic mesh body member affixed to the ramus or ramus stump. Over the years the Hahn mandibular prostheses for condyle replacement have been found to be expensive to manufacture and difficult to install and adjust to proper TMJ alignment. Most importantly, such prostheses have experienced unfavorable short-term and long-term biocompatibility and wear resistance of the materials of construction in and under the TMJ environment.

In 1988, T. A. Collins was granted U.S. Pat. No. 4,726,808 disclosing mandibular prostheses comprised of pairs of spaced (substantially parallel) metal strips which are joined together at one end and are placed on opposite sides of mandibular bone stumps that may remain on one side of damaged areas of the mandible. The opposing metal strips are each provided with alternating threaded and non-threaded holes. The non-threaded holes of one strip are oriented so as to oppose the threaded holes of the other strip so that screws can be extended between the strips (through drilled holes of the intermediate mandibular bone) from a non-threaded hole of one strip to a threaded hole of the opposing strip. In one disclosed form, the Collins mandibular prosthesis includes, at the joined end of a set of the parallel metal mounting strips, an attached metallic artificial condyle. A sleeve of silicone or other suitable plastic material is applied over the condyle. It has been well established that Collins-type condyle replacement protheses: are difficult to install because screw hole alignment is not maintained when contouring of the strips is required, provide no means for adjusting the orientation of the condyle head to match the cup-shape of the glenoid fossa, and include condyle head materials that are objectionable in the TMJ environment.

It is an important object of the present invention to provide a mandibular prosthesis for repair and replacement of the condylar process of the human mandible that can be surgically implanted more quickly, easily and safely than the prostheses that are presently available.

It is another important object of the invention to provide a mandibular prosthesis for repair and replacement of the condylar process of the TMJ complex that is constructed of biocompatible materials and can be readily adjusted to proper condyle head orientation with respect to the glenoid fossa.

It is a further object of the invention to provide a mandibular prosthesis for repair and replacement of the condylar process which is of relatively simple and economic construction from materials which have been established as structurally suitable and biocompatible under high stress and force conditions of the type experienced by the TM joint of humans.

Other objects and advantages of the invention will become apparent through the following specification when considered in the light of the attached drawing figures.

SUMMARY OF THE INVENTION

The present invention relates to a mandibular prosthetic appliance for the repair and replacement of the condylar process of the human mandible. More specifically, the invention relates to a biocompatible, structurally sound, mandibular prosthesis structure (hereinafter referred to as a "condylar replacement prosthesis") for the repair and replacement of the condylar process or condyle component of the temporomandibular joint (TMJ) complex. The TM joint complex on each side of the mandible is basically comprised of the knob-shaped condyle prominence of the ramus, the meniscus, the cup-shaped glenold fossa formed in the temporal bone of the skull, and supporting and connecting structures.

The unique condylar replacement prosthesis of the invention is comprised of an upper synthetic condyle replacement member, including its supporting stem portion, and a lower perforated metal ramus attachment fixture within which the stem portion of the condylar replacement member is adjustably positioned and retained. The synthetic condylar replacement member, with its lower stem portion is preferably fabricated of "Delrin" acetal resin. Delrin (a registered trademark of DuPont de Nemours Co.) is a thermoplastic polymer of the polyacetal family of compounds with the chemical name polyoxymethylene or polyformaldehyde. This material has been widely used in engineering in applications requiring strength, creep resistance, and stability over time. In the medical field Delrin has been found to be non-toxic and biocompatible with respect to hard and soft tissues of the human body and the material has been used for many years in total hip replacement procedures with only a few instances of material rejection or required removal because of excessive wear. The knob-shaped head portion of the synthetic condylar replacement member of the invention is provided in a series of typical condyle shapes and sizes for proper selection and fitment with respect to the glenoid fossa by the surgeon during the prosthesis placement surgical procedure.

The ramus attachment fixture of the present condylar replacement prosthesis is preferably fabricated from a panel of relatively thin perforated biocompatible metallic sheet material, particularly titanium mesh sheet material. Pure titanium is recognized as an unequaled implant material in use clinically for over 30 years with no documented cases of allergic reaction. Further, pure titanium is the material of choice in craniofacial reconstructive surgery when non-removal of the implanted prosthesis is indicated. As an implantable material, pure titanium is preferred because its low density (weight) and elastic modulus (stiffness) characteristics are approximately one-half that of stainless steel and cobalt-chrome alloys and the material is corrosion resistant and pliable.

A preferred form of perforated titanium mesh sheet material, for fabrication of the ramus attachment fixture of the present invention, is sheet material with substantially square perforations arranged uniformly in rows and lines so that bone screws may be applied through the perforations and into underlying bone without significant protrusion of the head portion of such screws, Alternatively, the perforated titanium mesh sheet material forming the ramus attachment fixture may include chamfered square and round screw holes arranged in uniform rows and lines.

The perforated metallic mesh ramus attachment fixture of the condylar replacement prosthesis of the present invention is formed with:

i) a cylindrical sleeve portion (for seating of the stem portion of the synthetic condyle replacement member) extending along the length of the posterior edge of the fixture;

ii) an outer ramus mount panel projecting forwardly from the sleeve portion (in a plane tangent to such sleeve portion) for bone screw attachment of the fixture to the ramus at the lateral side thereof;

iii) an upper panel portion extending forwardly from the upper sleeve portion (closing the upper peripheral portion of the cylindrical sleeve) adjacent the ramus mount panel and affixed thereto for attachment with the ramus mount panel to the ramus; and iv) a lower ramus clamping panel portion extending forwardly from the lower portion of the sleeve and spaced from the ramus mount panel for positioning on the medial side of the ramus and stabilizing the condylar replacement prosthesis in its mounted position on the ramus stump.

Surgical placement of the condylar replacement prosthesis of the invention involves the following procedures:

a) The synthetic condylar replacement member (with its condyle head size and shape appropriately selected for fitment to the glencid fossa) of the replacement prothesis is inserted (in its cylindrical stem portion) into the matching cylindrical sleeve portion of the ramus attachment fixture.

b) The ramus attachment fixture is mounted in appropriate TMJ orientation to the ramus stump via bone screws applied through selected mesh perforations of the ramus mount panel and into the lateral side of the ramus stump. Positioning of the attachment fixture must be such that the bottom surface of the stem portion of the synthetic condylar replacement member will interface with and rest upon the upper surface of the horizontal step in the ramus as surgically prepared by the surgeon.

c) The lower ramus clamping panel of the fixture is pinched inwardly into contact with the medial side of the ramus stump for stabilization of the fixture with respect to the ramus.

d) The synthetic condyle replacement member of the replacement prosthesis (with its stem portion resting on the step cut in the ramus) is adjusted in its rotational orientation within the supporting cylindrical sleeve portion of the attachment fixture.

e) Finally, one or more bone screws are applied through mesh perforations on the lateral side of the upper part of the fixture sleeve and into the stem portion of the condyle replacement member to lock the condyle replacement member in appropriate TMJ operating position.

BRIEF DESCRIPTION OF THE DRAWING FIGURES

FIG. 1 is a side view of a human skull showing the mandible (lower jaw bone) with the artificial condylar replacement prosthesis of the invention shown in place attached to the ramus portion of the mandible on the left side thereof;

FIG. 2 is an enlarged perspective view of the mandible of the skull of FIG. 1 showing in greater detail the artificial condylar replacement prosthesis mounted to the ramus on the left side of the mandible and showing the right side condylar process severed from the right side ramus;

FIG. 3 is a medial view of the left ramus of the mandible of FIG. 2 with the artificial condylar replacement prosthesis mounted thereto;

FIG. 4 is a longitudinal view of the medial side of the artificial condylar replacement prosthesis of the invention;

FIG. 5 is an exploded view of the components of the artificial condylar replacement prosthesis of FIG. 4 showing the synthetic condyle replacement member, with its lower stem portion, and the ramus attachment fixture of the prosthesis unit;

FIG. 6 is a cross section view of the ramus attachment fixture of FIG. 5 taken on line 6—6 of FIG. 5; and FIG. 7 is a top view of the ramus attachment fixture of FIG. 5.

DESCRIPTION OF THE PREFERRED EMBODIMENT

Referring initially to FIG. 1 there is illustrated a human skull 10 showing the mandible (lower jaw bone) 12 in its closed position and as having a generally horizontal body portion with an anterior prominence (mandibular symphysis) 14 defining the chin in the facial structure. A branch of the mandible or ramus portion 16 extends upwardly and rearwardly at the posterior end of the body portion of the mandible. As shown in FIG. 2, the mandible 12 is U-shaped with like posterior ramus portions 16. The upper section of the ramus portions of the normal human mandible terminate in a rearward condyloid process or condyle 18 (the right condyle being shown severed from its ramus portion) and a forward coronoid process 20, the condyloid process and coronoid process being separated by the sigmoid notch 22.

In accordance with the present invention (and as shown in FIGS. 1 and 2), there is affixed to the left-side ramus an artificial condylar replacement prosthesis 30 which is described in detail hereinafter. These figures show the lateral side of the mounted prosthesis. FIG. 3 is a medial (inside) partial view of the left-side ramus 16 of the mandible 12 of FIG. 2 with the artificial condylar replacement prosthesis 30 mounted thereto and shows the medial side of the mounted prosthesis.

FIG. 4 is a longitudinal view of the medial side of the assembled artificial condylar replacement prosthesis 30 per se and FIG. 5 is an exploded view of the prosthesis showing the two components thereof, i.e., the upper synthetic condylar replacement member 32 and the lower ramus attachment fixture 34. The condylar replacement member 32 is preferably fabricated of "Delrin" acetal resin and is comprised of an upper knob-shaped head portion 32a and a lower stem portion 32b. As previously indicated, the knob-shaped head portion 32a of the replacement member is provided in a series of shapes and sizes to replicate natural human condyles for proper fitment with respect to the glenold fossa of the TM joint complex. Selection of the appropriate condylar replacement member is made by the surgeon from x-ray, MRI and CT scans of the natural condyle of the patient with final selection determination by the surgeon during the prosthesis placement surgical procedure.

The ramus attachment fixture 34 of the condylar replacement member 30 is, as previously indicated, preferably fabricated from thin perforated biocompatible metallic sheet material, particularly titanium mesh sheet material. In the figures the attachment fixture is shown to be fabricated of perforated metallic sheet material in which the perforations are substantially square openings arranged uniformly in rows and lines. As clearly shown in FIGS. 4 and 5, the ramus attachment fixture 34 is comprised of an outer ramus mounting panel 36, a cylindrical sleeve portion 38, an upper panel portion 40 extending from the upper sleeve portion, and a lower ramus clamping panel portion 42. FIG. 6 is a cross section view of the ramus attachment fixture 34 of FIG. 5 taken on line 6—6 of FIG. 5 showing the relationship of the mounting panel portion 36 and clamping panel portion 42 with respect to the cylindrical sleeve portion 34, FIG. 7 is a top view of the ramus attachment fixture 34 of FIG. 5 showing the closed upper cylindrical sleeve portion 38 (holds the stem portion 32b of the condylar replacement member 32) and upper panel portion 40.

The cylindrical sleeve portion 38 of attachment fixture 34 is for seating the stem portion of the synthetic condyle replacement member 32 and extends along the length of the proximal edge of the fixture. The outer ramus mounting panel 36 projects forwardly from the sleeve portion 38 in a plane substantially tangent to the sleeve portion. The upper panel portion 40 of the fixture extends forwardly from the upper sleeve portion and closes the upper peripheral portion of the sleeve 38. The panel portion 40 rests in interfacing contact with the mounting panel 36, as shown in the top view of FIG. 7, with its perforations in alignment with the perforations of panel 36. The lower ramus clamping panel 42 extends forwardly from the lower portion of the sleeve portion 38 of fixture 34 and is spaced from the ramus mounting pane 36 for positioning on the medial side of the ramus stump for stabilizing the condylar replacement prosthesis 30 in its mounted position on the ramus stump.

Surgical placement of the condylar replacement prosthesis of the invention involves the following procedures:

a) The synthetic condylar replacement member 32 of the replacement prosthesis 30 (with the head portion 32a of the replacement member appropriately selected for fitment to the glenoid fossa of the TN joint complex) is inserted (in its cylindrical stem portion 32b) into the matching cylindrical sleeve portion 38 of the ramus attachment fixture 34. As such, the replacement member may be adjustably rotated and positioned vertically within the sleeve.

b) The ramus attachment fixture 34 is mounted in appropriate TMJ orientation to the ramus stump 16 via bone screws 50 applied through selected mesh perforations of the ramus mounting panel 36 of the fixture and into the lateral surface of the stump. In practice, a first bone screw is applied and tightened only to the extent that the condylar replacement member 32 of the fixture 34 can be rotationally moved to a position whereat proper polar axis alignment of the condyle replacement member 32 is achieved with respect to the glencid fossa of the TM joint complex. After such alignment additional bone screws are applied and tightened to a proper torque extent.

c) The lower ramus clamping panel 42 of the ramus attachment fixture 34 is pinched inwardly into contact with the medial side of the ramus stump for stabilization of the fixture with respect to the ramus.

d) The synthetic condyle replacement member 32 of the replacement prosthesis 30 is adjusted to its final rotational orientation within the supporting cylindrical sleeve portion 38 of the attachment fixture 34 so that the artificial head portion 32a thereof is in proper position in the TM joint complex for proper operation of the mandible.

e) Finally, one or more bone screws 52 are applied through the mesh perforations on the lateral side of the upper part of the sleeve portion 38 of the attachment fixture 34 and into the stem portion 32b condyle replacement member 32 to lock the replacement member 32 in its proper position.

As previously indicated, FIG. 2 has shown the human mandible 12 as U-shaped with two like ascending ramus portions 16. Upon the left side of the illustrated mandible is mounted a left-side condylar replacement prosthesis 30 in accordance with the present invention. The posterior right side of the mandible is shown to have the right-side condylar process 18 severed from the ramus 16, leaving a ramus stump portion 16a cut with a horizontal plateau, in preparation for the placement of a right-side condylar replacement prosthesis (not shown). A right-side condylar replacement prosthesis would, in accordance with the invention, comprise a mirror image of the prosthesis shown in FIGS. 1–7. With the ramus stump 16a prepared as shown, a mirror image prosthesis would be seated on the ramus with the lower edge of the upper closed cylindrical sleeve portion of the prosthesis abutting the horizontal plateau cut of the ramus stump and the mounting panel and clamping panel of the prosthesis straddling the ramus.

While the invention has been described in connection with a particular structural embodiment of a mandibular prosthesis for replacement of a diseased or fractured condylar process portion of the TM joint complex of a human mandible, many modifications of the invention will be apparent to those skilled in the art. Accordingly, such modifications are to be included within the spirit and scope of the invention as defined by the following claims.

What is claimed is:

1. Mandibular prosthesis apparatus for mounting on the remaining stump portion of the ascending ramus, at the posterior end of a human mandible, from which has been removed by surgical intervention a diseased or fractured condylar process portion of said ramus as part of the TM joint complex of said mandible comprising:

a synthetic condylar replacement member formed of a non-toxic, biocompatible thermoplastic polymer of the polyacetal family of compounds and including an upper knob-shaped condyle portion and a lower cylindrical condyle-supporting stem portion; and a ramus attachment fixture for receiving the cylindrical condyle-supporting stem portion of said condylar replacement member, attachment to said ramus stump, and adjustably supporting said replacement member in proper polar axis alignment in said TH joint complex, said attachment fixture formed of tissue-biocompatible titanium sheet material having perforations therethrough for receiving bone screws to affix said fixture to the stump portion of the ramus of said mandible and for fixing the position of said stem portion of said condylar replacement member therein for proper rotational orientation of said knob-shaped condylar portion of said replacement member in said TN joint complex, and said attachment fixture including,
i) a cylindrical sleeve portion for receiving in its upper section said cylindrical stem portion of said condylar replacement member and for the bone screw affixation of said stem portion to said attachment fixture,
ii) a ramus mount panel extending forwardly from said sleeve portion for bone screw attachment of said fixture to the stump portion of the ramus of said mandible at the lateral side thereof, and
iii) a ramus clamping panel portion extending forwardly from the lower section of said sleeve portion and spaced from the ramus mount panel positioned on the medial side of the stump portion of the ramus for stabilizing the condylar replacement prosthesis in its mounted position on the stump portion of the ramus.

2. Mandibular prosthesis apparatus for mounting on the remaining stump portion of the ascending ramus, at the posterior end of a human mandible, from which has been removed by surgical intervention a diseased or fractured condylar process portion of said ramus as part of the TM joint complex of said mandible, said stump portion presenting a surgically prepared substantially horizontal plateau, and said apparatus comprising:

a) a synthetic condylar replacement member formed of a non-toxic, biocompatible thermoplastic polymer of the pplyacetal family of compounds and including an upper knob-shaped condyle portion and a lower cylindrical condyle-supporting stem portion;

b) a ramus attachment fixture including a cylindrical sleeve portion for receiving the cylindrical condyle-supporting stem portion of said condylar replacement member and panel means for attaching said fixture to the stump portion of said ramus, said attachment fixture being formed of tissue-biocompatible, mesh-type perforated titanium sheet material;

c) mounting means cooperative with said panel means for securing said attachment fixture to the stump portion of said ramus, said mounting means comprising bone screws applied through the perforations of said titanium sheet material and into said ramus stump portion; and d) securing means cooperative with the cylindrical sleeve portion of said attachment fixture and said stem portion of said condylar replacement member for maintaining the knob-shaped condyle portion of said replacement member in proper rotational orientation in the TM joint complex of said mandible, said securing means comprising bone screws applied through the perforations of said titanium sheet material of said sleeve portion and into said stem portion, 3. The mandibular prosthesis apparatus for mounting on the remaining stump portion of the ascending ramus, at the posterior end of a human mandible, as claimed in claim 2 wherein the lower cylindrical condyle-supporting stem portion of said synthetic condylar replacement member is provided with a substantially flat bottom surface for seating on the substantially horizontal plateau of the stump portion of said ramus.

4. The mandibular prosthesis apparatus for mounting on the remaining stump portion of the ramus, at the posterior end of a human mandible, as claimed in claim 2 wherein the panel means of the ramus attachment fixture for attaching said fixture to the stump portion of the ramus projects forwardly from the cylindrical sleeve portion of said fixture for positioning and mounting on the lateral side of said stump portion of the ramus.

5. Mandibular prosthesis apparatus for mounting on the remaining stump portion of the ascending ramus, at the posterior end of a human mandible, from which has been removed by surgical intervention a diseased or fractured condylar process portion of said ramus as part of the TM joint complex of said mandible comprising:

a) a synthetic replacement member formed of a non-toxic, biocompatible thermoplastic polymer of the polyacetal family of compounds and including an upper knob-shaped condyle portion and a lower cylindrical condyle-supporting stem portion;

b) a ramus attachment fixture including:
i) a cylindrical sleeve portion for receiving the cylindrical condyle-supporting stem portion of said condylar replacement member,
ii) panel means for attaching said fixture to the stump portion of said ramus, said panel means projecting forwardly from said cylindrical sleeve portion of said fixture for positioning and mounting on the lateral side of said stump portion of the ramus, and
iii) a ramus clamping panel projecting forwardly from said cylindrical sleeve portion of said fixture and spaced from said panel means for positioning on the medial side of said stump portion of the ramus for stabilizing said condylar replacement prosthesis in its mounted position on said stump portion of the ramus;

c) mounting means cooperative with said panel means for securing said attachment fixture to the stump portion of said ramus, said mounting means comprising bone screws applied through the perforations of said titanium sheet material and into said ramus stump portion; and d) securing means cooperative with the cylindrical sleeve portion of said attachment fixture and said stem portion of said condylar replacement member for maintaining the knob-shaped condyle portion of said replacement member in proper rotational orientation in the TM joint complex of said mandible, said securing means comprising bone screws applied through the perforations of said titanium sheet material of said sleeve portion and into said stem portion.

* * * * *